United States Patent
Liao et al.

(10) Patent No.: US 12,105,006 B2
(45) Date of Patent: Oct. 1, 2024

(54) GAS DETECTION SYSTEM FOR GYNECOLOGICAL DISEASE DETECTION AND DETECTION METHOD USING THE SAME

(71) Applicant: AINOS, INC., San Diego, CA (US)

(72) Inventors: Chia-Nan Liao, Miaoli County (TW); Chia-Pin Huang, Miaoli County (TW); Tzu-Ting Weng, Miaoli County (TW); Yu-Hsuan Liao, Miaoli County (TW); Chun-Hsien Tsai, Miaoli Couty (TW); Ting-Chuan Lee, Miaoli County (TW); Chun-Jung Tsai, Miaoli County (TW)

(73) Assignee: AINOS, INC., San Diego, CA (US)

( * ) Notice: Subject to any disclaimer, the term of this patent is extended or adjusted under 35 U.S.C. 154(b) by 731 days.

(21) Appl. No.: 17/235,399

(22) Filed: Apr. 20, 2021

(65) Prior Publication Data
US 2022/0299418 A1    Sep. 22, 2022

(30) Foreign Application Priority Data
Mar. 16, 2021  (TW) ................................ 110109371

(51) Int. Cl.
*A61B 5/00*  (2006.01)
*B01L 3/00*  (2006.01)
(Continued)

(52) U.S. Cl.
CPC ........... *G01N 15/10* (2013.01); *A61B 5/4337* (2013.01); *B01L 3/502715* (2013.01); *G01N 15/0656* (2013.01); *A61B 2010/0083* (2013.01); *G01N 2015/1006* (2013.01); *G01N 2015/1022* (2024.01); *G01N 2015/1024* (2024.01)

(58) Field of Classification Search
CPC ............... G01N 15/10; G01N 15/0656; G01N 2015/1006; G01N 2015/105; G01N 2015/1062; G01N 33/497; G01N 33/0009; G01N 1/24; G01N 2015/1012; B01L 3/502715; A61B 2010/0083; A61B 5/14546; A61B 5/4318; A61B 10/00;
(Continued)

(56) References Cited

FOREIGN PATENT DOCUMENTS

| CN | 109715076 A | * | 5/2019 | ......... A61B 10/0038 |
| DE | 69732233 T2 | * | 12/2005 | ............. A61B 5/145 |
| GB | 2479984 A | * | 11/2011 | ......... A61B 5/14539 |

* cited by examiner

*Primary Examiner* — Robert R Raevis
(74) *Attorney, Agent, or Firm* — Muncy, Geissler, Olds & Lowe, P.C.

(57) ABSTRACT

A gas detection system for gynecological disease detection and a detection method using the same are provided. The gas detection system is configured to detect an analyte from a female vagina and includes a main body, a sleeve, a detector, a pump, and a controller. The main body includes a body portion and a head portion having an intake channel. The body portion includes a detection chamber and an exhaust channel. The detector includes at least one sensor configured to detect at least one target of the analyte and produce at least one detection signal. The pump is communicated with the detection chamber and the exhaust channel. The controller includes a processing unit and a first communication unit. The processing unit receives the at least one detection signal and controls the first communication unit to send the at least one detection signal.

14 Claims, 9 Drawing Sheets

(51) Int. Cl.
*G01N 15/06* (2006.01)
*G01N 15/10* (2006.01)
*A61B 10/00* (2006.01)

(58) Field of Classification Search
CPC ... A61B 5/14507; A61B 5/207; A61B 5/4337; A61B 5/4294; A61B 5/14514
USPC ..... 73/1.03, 1.06, 19.1, 23.2, 23.34, 863.01, 73/863.34, 864.73, 864.81, 431; 600/574, 600/350, 360, 363, 591
See application file for complete search history.

GAS DETECTION SYSTEM FOR
GYNECOLOGICAL DISEASE DETECTION
AND DETECTION METHOD USING THE
SAME

BACKGROUND OF THE INVENTION

Field of the Invention

The present invention relates to a gas detection system for gynecological disease detection and a detection method using the same.

Description of the Prior Art

Generally, gynecological diseases related to female private parts are related to infection or inflammation of vagina or genitals, and three most common types of vaginal infections are candida vulvovaginitis (yeast infections), bacterial infections (bacterial vaginosis) and parasitic infections (trichomoniasis). Common symptoms of vaginal infections include vaginal odor, increasing or changing in the vaginal discharge, vaginal redness, itching, or pain, etc., which requires to be treated as soon as possible to avoid additional influences.

However, diagnosis of the gynecological diseases is usually applied by contact or invasive methods, which is easy to cause psychological and physical discomfort for the patient. Moreover, body fluid sampled from vagina has to be tested and cultured to determine cause of disease (such as species of bacteria or mold), which is time consuming, unsuitable for self-diagnostic and cannot obtain the diagnosis of the disease immediately.

The present invention is, therefore, arisen to obviate or at least mitigate the above-mentioned disadvantages.

SUMMARY OF THE INVENTION

The main object of the present invention is to provide a gas detection system for gynecological disease detection and a detection method using the same, which provides contactless detection and can rapidly obtain detection results.

To achieve the above and other objects, the present invention provides a gas detection system for gynecological disease detection, configured to detect an analyte from a female vagina, including: a main body, a sleeve, a detector, a pump, and a controller. The main body includes a body portion and a head portion protrudingly disposed on the body portion. The head portion has an intake channel disposed therethrough and configured to input the analyte, and the body portion includes a detection chamber communicated with the intake channel and an exhaust channel. The sleeve is detachably sleeved to the head portion and includes a through slot aligned with the intake channel. The detector includes at least one sensor disposed in the detection chamber, and the at least one sensor is configured to detect at least one target of the analyte and produce at least one detection signal. The pump is disposed on the main body and communicated respectively with the detection chamber and the exhaust channel. The controller controls operation of the detector and the pump, and the controller includes a processing unit and a first communication unit communicated with the processing unit. The processing unit receives the at least one detection signal and controls the first communication unit to send the at least one detection signal.

To achieve the above and other objects, the present invention further provides a detection method using the gas detection system for gynecological disease detection as described above, including following steps of: sampling: putting an end of the gas detection system with the sleeve to be close to a female genital and starting the pump to input the analyte into the detection chamber; detection: detecting the at least one target and producing the at least one detection signal by the detector; output: outputting the at least one detection signal to an analysis module; and analysis: analyzing the at least one detection signal to obtain a detection result data by the analysis module.

The present invention will become more obvious from the following description when taken in connection with the accompanying drawings, which show, for purpose of illustrations only, the preferred embodiment(s) in accordance with the present invention.

Figure 1:
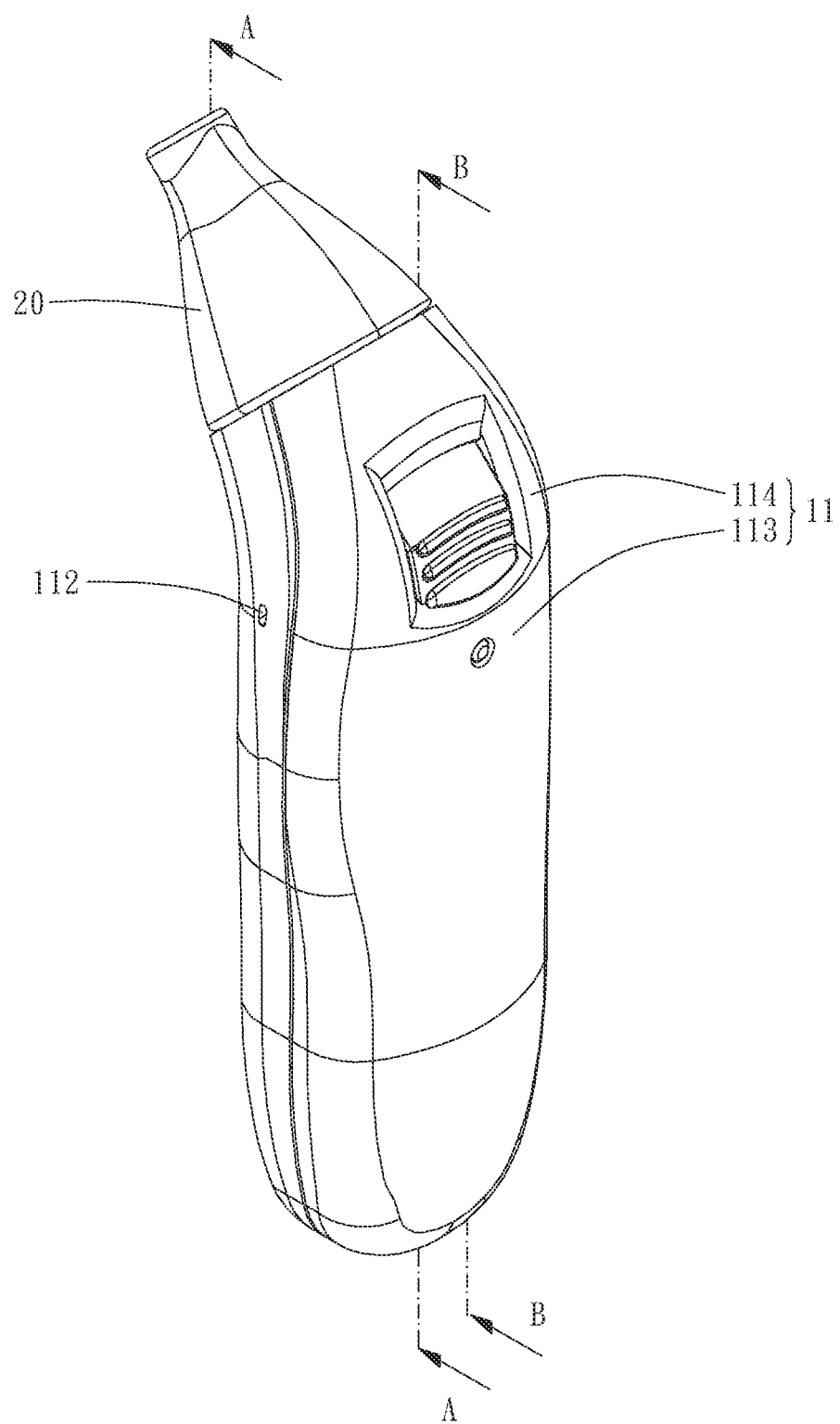
FIG. 1 is a stereogram of a preferable embodiment of the present invention.
Figure 2:
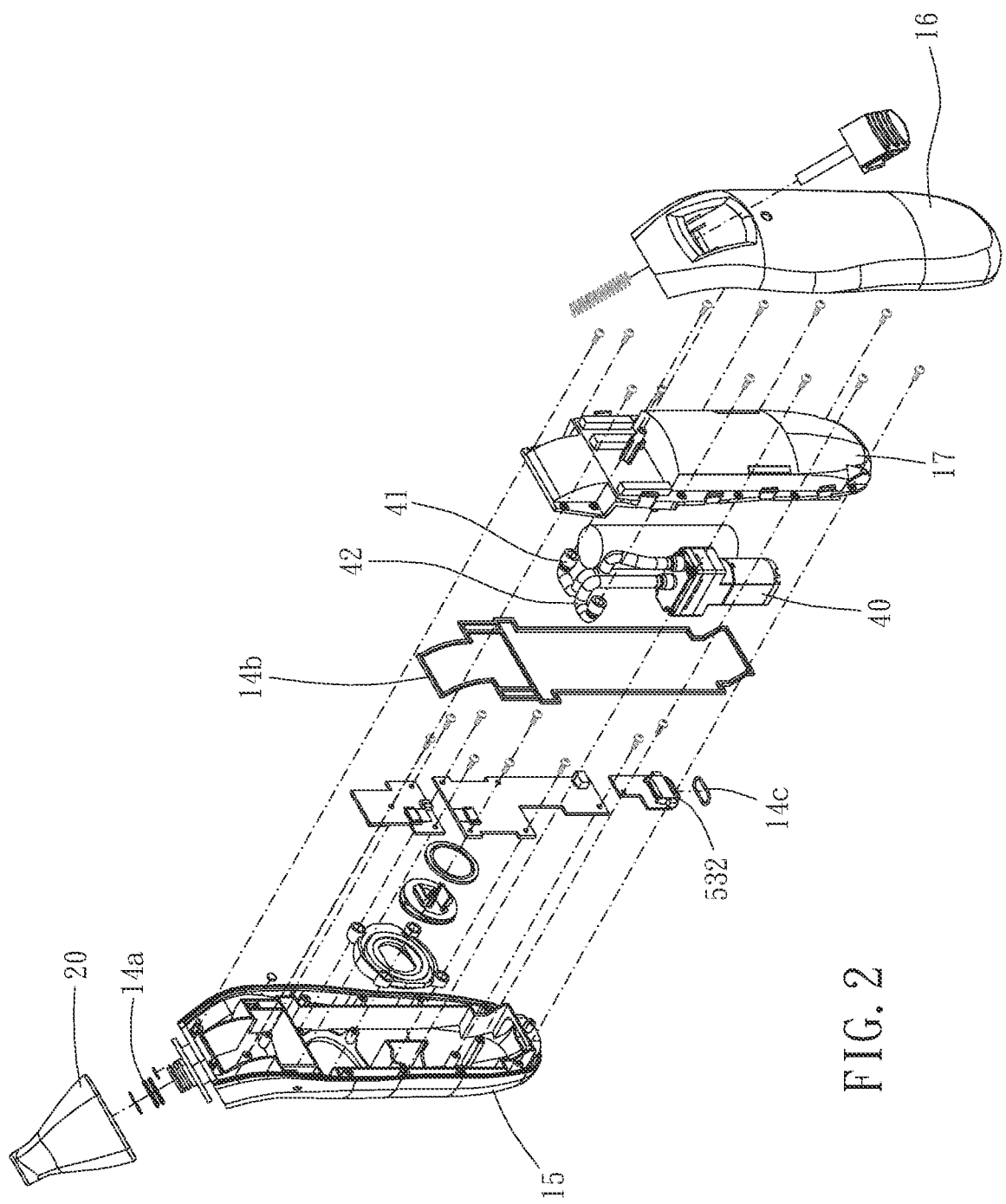
FIG. 2 is a breakdown drawing of a preferable embodiment of the present invention.
Figure 3:
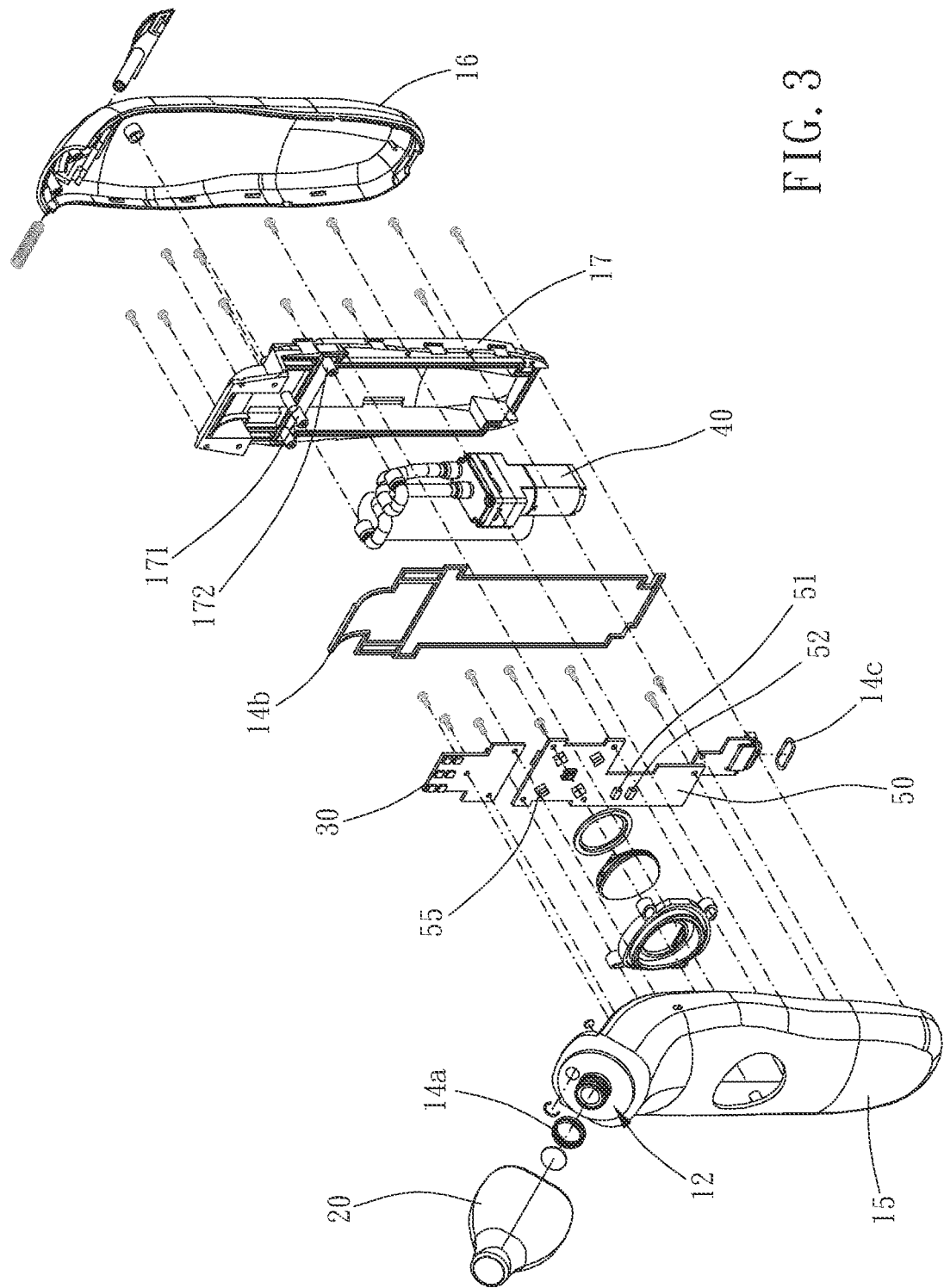
FIG. 3 is another breakdown drawing of a preferable embodiment of the present invention.
Figure 4:
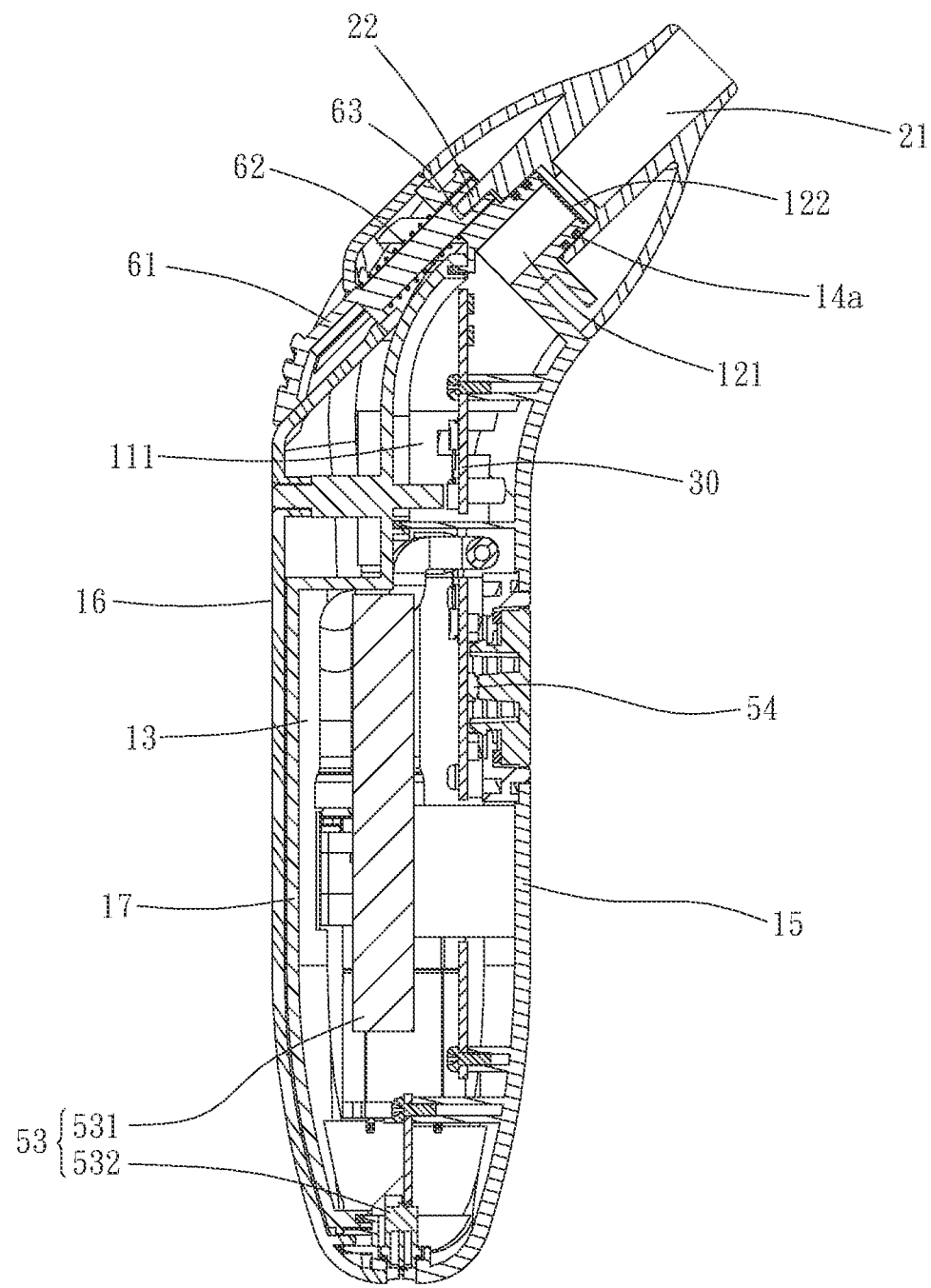
FIG. 4 is a cross-sectional view taken on A-A line of FIG. 1.
Figure 5:
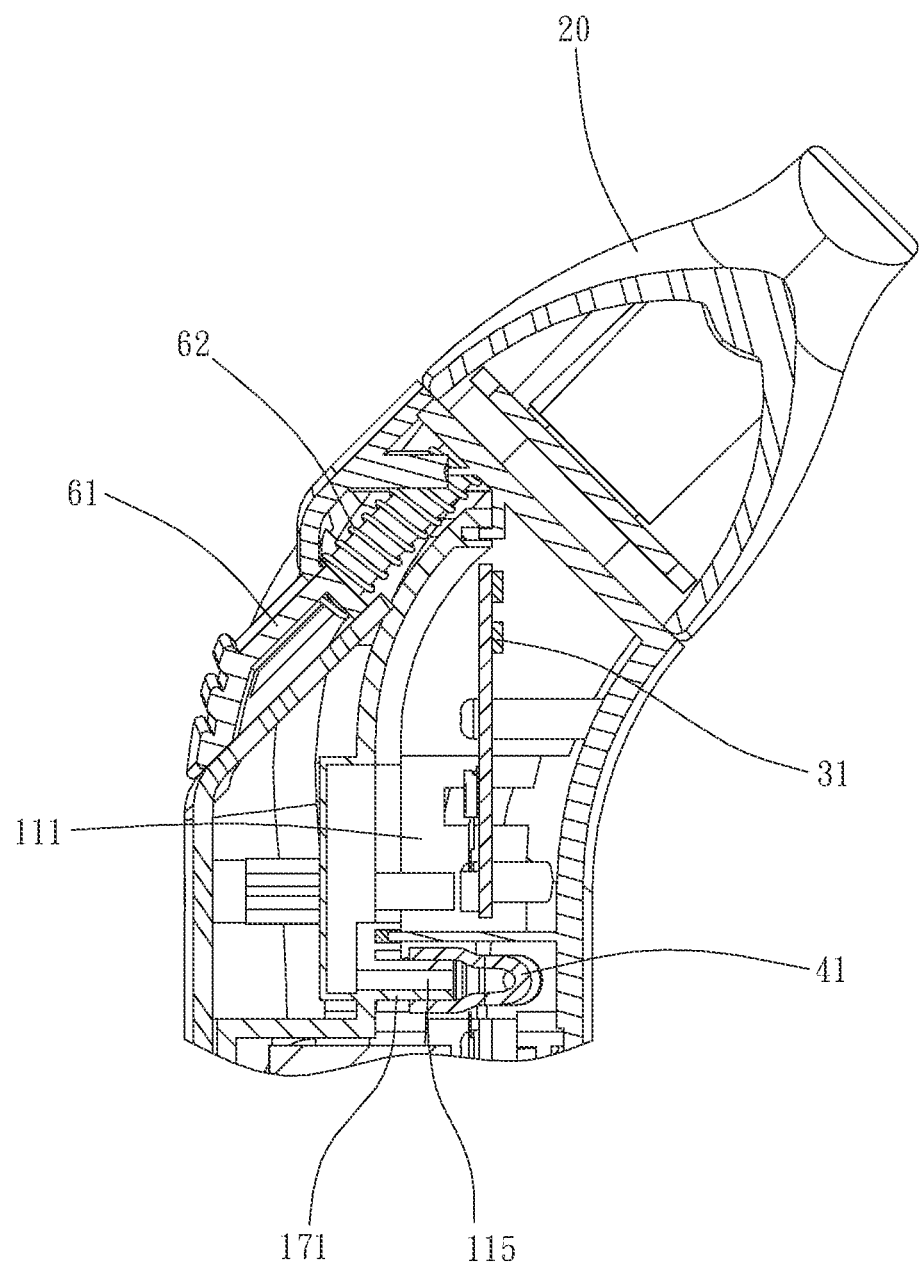
FIG. 5 is a partial cross-sectional view taken on B-B line of FIG. 1.

DETAILED DESCRIPTION OF THE
PREFERRED EMBODIMENTS

Please refer to FIGS. 1 to 9 for a preferable embodiment of the present invention. A gas detection system for gynecological disease detection of the present invention is configured to detect an analyte from a female vagina and includes a main body 10, a sleeve 20, a detector 30, a pump 40 and a controller 50.

The main body 10 includes a body portion 11 and a head portion 12 protrudingly disposed on the body portion 11. The head portion 12 has an intake channel 121 disposed therethrough and configured to input the analyte, and the body portion 11 includes a detection chamber 111 communicated with the intake channel 121 and an exhaust channel 112. The sleeve 20 is detachably sleeved to the head portion 12 and includes a through slot 21 aligned with the intake channel 121. The detector 30 includes at least one sensor 31 disposed in the detection chamber 111, and the at least one sensor 31 is configured to detect at least one target in the analyte and produce at least one detection signal. The pump 40 is disposed on the main body 10 and communicated respectively with the detection chamber 111 and the exhaust channel 112. The controller 50 controls operation of the detector 30 and the pump 40 and includes a processing unit 51 and a first communication unit 52 communicated with the processing unit 51. The processing unit 51 receives the at least one detection signal and controls the first communication unit 52 to send the at least one detection signal. The analyte is gas sampled from an area adjacent to female external genitalia. Generally, a composition of the gas is changed due to gas or metabolites produced by reproduction of bacteria or trichomoniasis. Therefore, the gas detection system is used to contactlessly collect, sense and analyze the analyte for quick detection of gynecological diseases.

The body portion 11 includes a straight segment 113 extending in an axial direction and a bent segment 114 from the straight segment 113 toward a side remote from the axial direction, and the head portion 12 is integrally connected with the bent segment 114. Therefore, the straight segment 113 is configured to be held by an operator, and the bent segment 114 is convenient for the head portion 12 to be directed toward a sampling area. For example, when the operator is sampling for others, the head portion 12 is put upward relative to the straight segment 113 and the intake channel 121 is directed toward the sampling area; when the operator is self-sampling, the head portion 12 is put downward relative to the straight segment 113 and the intake channel 121 is directed toward the sampling area. The gas detection system can be held in several ways for different states of operation.

Specifically, a diametrical dimension of the sleeve 20 is decreased in a direction remote from the head portion 12 so as to be convenient to be close to the sampling area. At least one of the sleeve 20 and the head portion 12 has a filter 122 covering the intake channel 121, which prevents foreign objects from entering the detection chamber 111. In this embodiment, an opening of the intake channel 121 has one said filter 122 which is a membrane being waterproof and gas permeable so as to avoid liquid infiltration and allow gas to flow therethrough.

Figure 7:
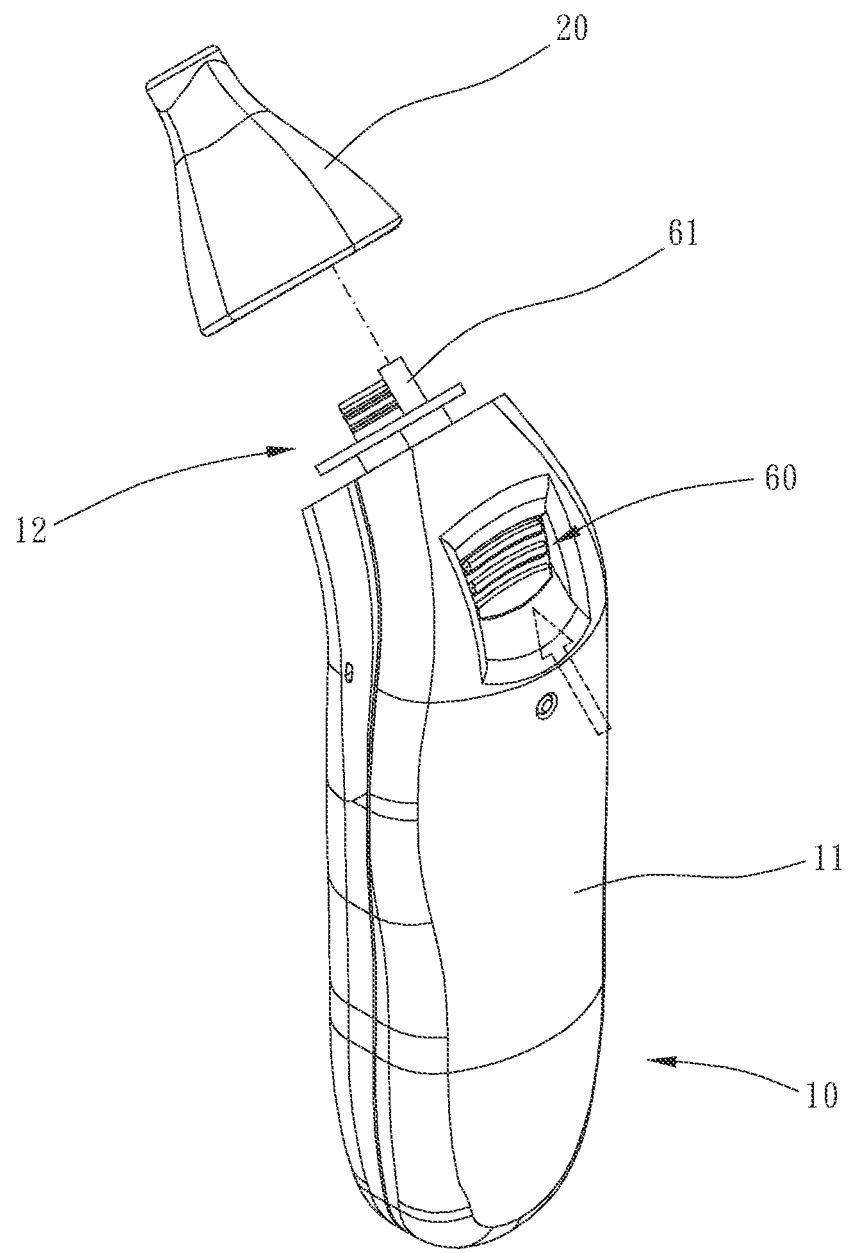
FIG. 7 is a schematic diagram showing operation according to a preferable embodiment of the present invention.
Figure 8:
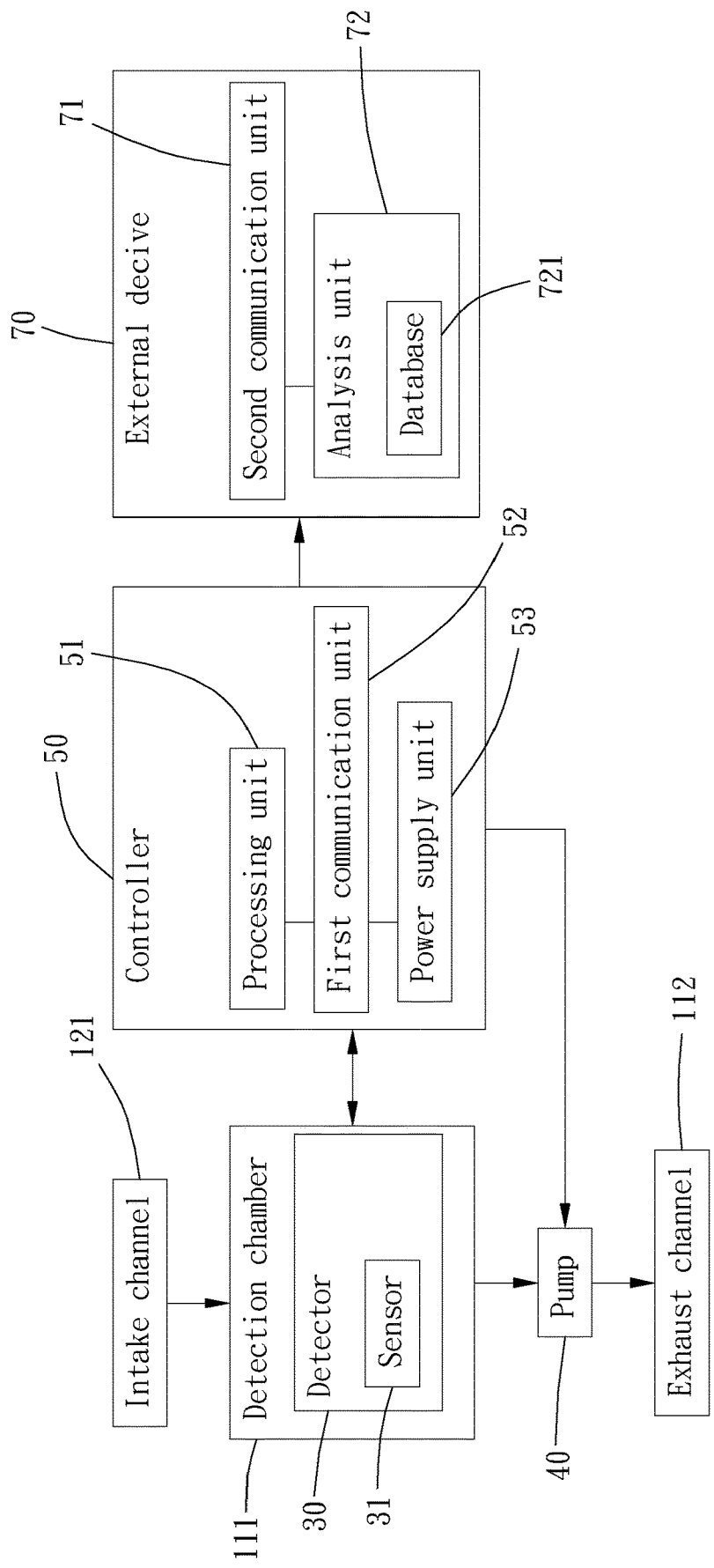
FIG. 8 is a block diagram of a preferable embodiment of the present invention.
Figure 9:
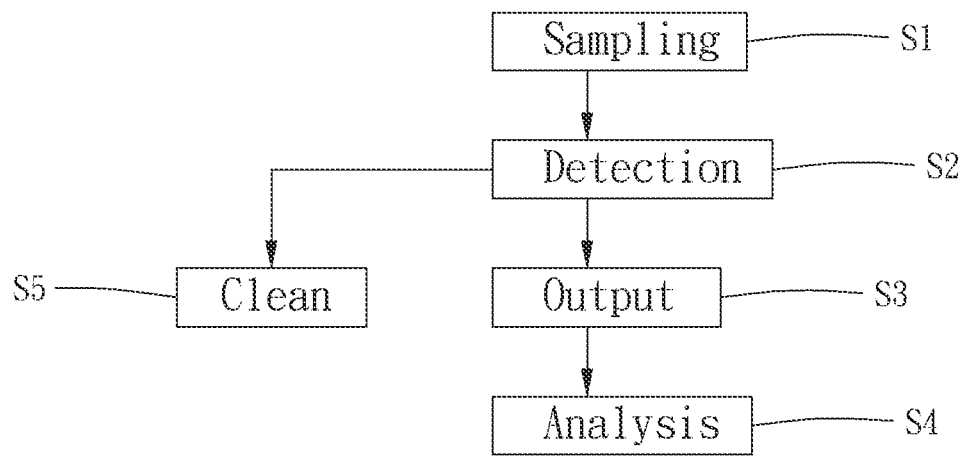
FIG. 9 is a flow chart of a preferable embodiment of the present invention.

The gas detection system further includes a withdrawal mechanism 60 disposed between the main body 10 and the sleeve 20. The withdrawal mechanism 60 includes an abutting member 61 disposed on the body portion 11, and the abutting member 61 is abuttable against the sleeve 20 to move the sleeve 20 in a direction remote from the head portion 12 (as shown in FIG. 7), which is convenient to replace the sleeve 20 for prevention of cross infection. Preferably, the withdrawal mechanism 60 further includes an elastic member 62 abutted against and between the main body 10 and the abutting member 61 so that the abutting member 61 can return automatically to an original position. The sleeve 20 preferably has a first engaging portion 22, and one of the abutting member 61 and the head portion 12 has a second engaging portion 63 being engageable with the first engaging portion 22, which is convenient to align and assemble with each other and prevents the sleeve 20 from being rotated relative to the head portion 12. In this embodiment, at least one first sealing member 14a is disposed between the sleeve 20 and the head portion 12 for easy assembling and good airtight effect; the first engaging portion 22 is a projection, the second engaging portion 63 is a recess disposed on the abutting member 61, and the projection is insertable into the recess so as to prevent the sleeve 20 from falling off directly when the abutting member 61 is actuated. In other embodiments, the sleeve and the head portion may be assembled with each other by magnetic attraction or snap-fit; the first engaging portion may be the recess, the second engaging portion may be the projection.

Figure 6:
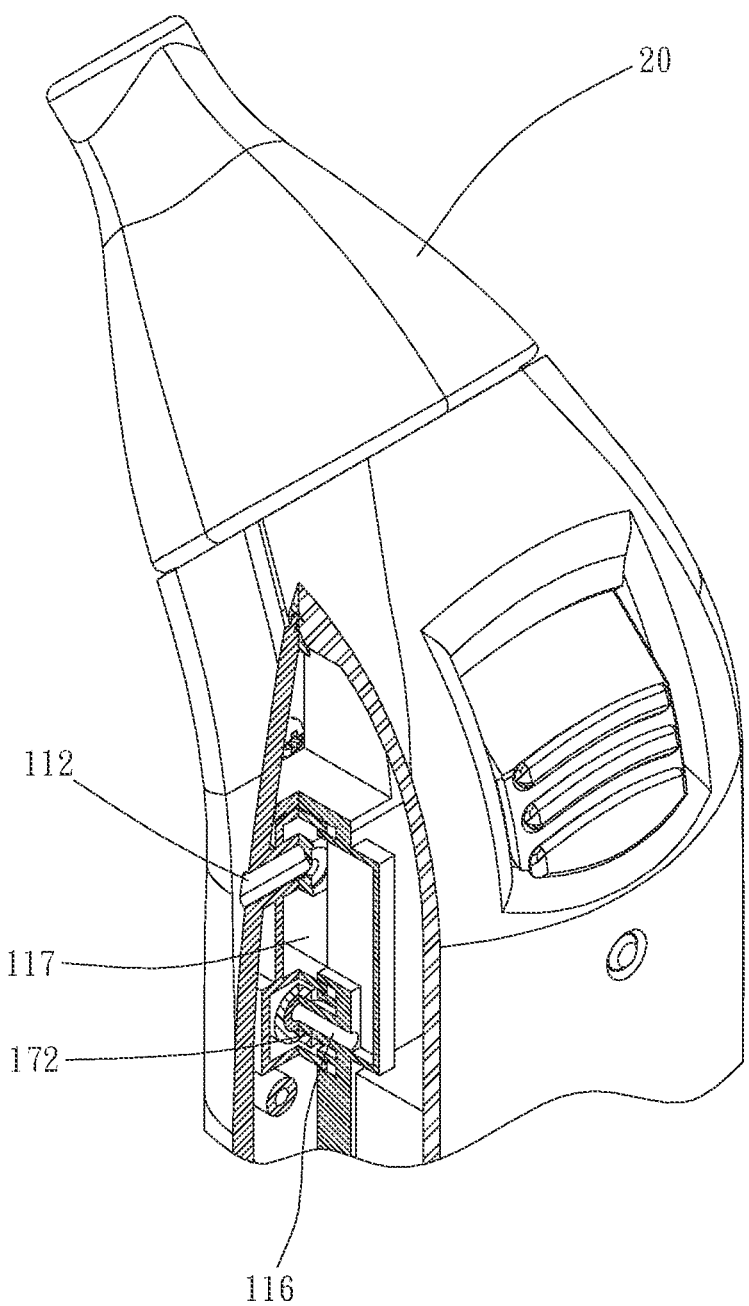
FIG. 6 is a partial cross-sectional view of a preferable embodiment of the present invention.

The main body 10 further includes a receiving chamber 13 and a first communication channel 115 communicated between the detection chamber 111 and the receiving chamber 13. The pump 40 and the controller 50 are disposed in the receiving chamber 13, and an inlet pipe 41 of the pump 40 is communicated with the first communication channel 115. The main body 10 further includes a second communication channel 116 communicated between the receiving chamber 13 and the exhaust channel 112, and an outlet pipe 42 of the pump 40 is communicated with the second communication channel 116, which is easy to be manufactured and assembled. Therefore, when the pump 40 is started up, the detection chamber 111 is formed negative pressure to input the analyte through the intake channel 121, and the analyte can be exhausted through the exhaust channel 112. In this embodiment, the pump 40 is a micropump that has a small volume and low power consumption. A transitional chamber 117 is disposed between the exhaust channel 112 and the second communication channel 116, as shown in FIG. 6, so that the analyte is appropriately detained for the at least one sensor 31 to detect the analyte when the pump 40 stops pumping. The second communication channel 116 and the exhaust channel 112 are lateral to each other and respectively communicated with the transitional chamber 117 so as to avoid rapid diffusion of the analyte. Preferably, the detection chamber 111, the first communication channel 115, the second communication channel 116 and the transitional chamber 117 are located at a side of the main body 10 adjacent to the head portion 12, which can effectively reduce configuration spaces and minimize a volume of the main body 10.

The main body 10 further includes a first housing 15, a second housing 16 and a third housing 17 disposed between the first housing 15 and the second housing 16. The first housing 15 and the third housing 17 define the detection chamber 111, the receiving chamber 13 and the transitional chamber 117 therebetween, which is convenient for arrangement of interior components. Preferably, a second sealing member 14b is disposed between the first housing 15 and the third housing 17, and a shape of the second sealing member 14b at least partially corresponds to shapes of the detection chamber 111, the receiving chamber 13 and the transitional chamber 117 so that the detection chamber 111, the receiving chamber 13 and the transitional chamber 117 are airtightly separated from one another. The third housing 17 has a first pillar 171 located between the detection chamber 111 and the receiving chamber 13 and a second pillar 172 located between the transitional chamber 117 and the receiving chamber 13, and the first pillar 171 and the second pillar 172 extend respectively toward the first housing 15. respectively toward the first housing 15. The first communication channel 115 extends through the first pillar 171, and the second communication channel 116 extends through the second pillar 172, which is easy to be manufactured and assembled and effectively reduces space required for configurations of gas channels.

The controller 50 further includes a power supply unit 53 electrically connected with the processing unit 51, and the power supply unit 53 includes a battery 531 received in the receiving chamber 13 and an electrical interface 532 configured to be connected with an external power source. The electrical interface 532 may preferably be used to transfer the at least one detection signal. Preferably, a third sealing member 14c is disposed between the electrical interface 532 and the main body 10 so as to avoid liquid infiltration and be convenient for clean and sterilization. Specifically, the controller 50 further includes a switch 54 and a prompt portion 55 electrically connected with the processing unit 51. In this embodiment, the switch 54 is a push-button switch; when the switch 54 is actuated, the processing unit 51 controls the pump 40 and the detector 30 to operate and the prompt portion 55 produces at least one prompting signal so that the operator can confirm a state of the gas detection system. In this embodiment, the prompt portion 55 includes a plurality of lighting members. For example, but not limited to, when the gas detection system is detecting, the processing unit 51 controls the plurality of lighting members to emit steady light; when the gas detection system battery is low, the processing unit 51 controls the plurality of lighting members to change light colors. However, the prompt portion may be an audio device or vibration device.

The gas detection system further includes an analysis unit 72 communicated with the processing unit 51, and the analysis unit 72 obtains a detection result data according to the at least one detection signal. In this embodiment, the gas detection system further includes an external device 70, and the external device 70 includes the analysis unit 72 and a second communication unit 71 wirelessly communicated with the first communication unit 52. The external device 70 may be an electronic device, such as smart phones, tablets, laptops, etc., for quick analysis and reading of the detection result data, and the wireless communication method includes at least one of radio waves, infrared, Bluetooth, Wi-Fi and the Internet. The analysis unit 72 further includes a database 721 storing a plurality of standard gas graphs, and the analysis unit 72 may covert the at least one detection signal into a gas graph by artificial intelligence (AI) algorithm and compare the gas graph with the plurality of standard gas graphs to obtain the detection result data. In this embodiment, the at least one sensor 31 contacts a plurality of gas molecules (a plurality of said targets) in the analyte to generate a plurality of electric signals (a plurality of said detection signals), and the analysis unit 72 converts the plurality of said electric signals into a composition and content of the analyte to form the gas graph, which provides good recognition and fast response rate. Each of the plurality of standard gas graphs is obtained by detecting a standard gas whose composition is known (analysis results of clinical trials, for example) and is pre-established in the database 721. The database 721 is preferably a cloud database, and the external device 70 has an application (APP) disposed thereon and being wirelessly connectable with the database 721 so as to access related data. The APP may upload the detection result data to a cloud server so as to be accessible by medical institutions for remote diagnosis. The plurality of said targets may include gas molecules, such as hydrogen sulfide, ammonia, carbon monoxide, carbon dioxide, and volatile organic compounds (TVOC); each of the plurality of standard gas graphs corresponds to at least one related disease. In other embodiments, the main body and the external device may be in a wired connection; the analysis unit may be disposed in the main body without the external device, and the main body may further has a display device communicated with the processing unit so that the processing unit can control the display device to show related information according to the detection result data of the analysis unit; and the processing unit may control the first communication unit to send the detection result data to an external access unit for reading or retention.

The present invention further provides a detection method using the gas detection system as described above, including following steps of: sampling S1: putting an end of the gas detection system with the sleeve 20 to be close to a female genital and starting the pump 40 to input the analyte into the detection chamber 111; detection S2: detecting the at least one target and producing the at least one detection signal by the detector; output S3: outputting the at least one detection signal to the analysis unit 72; and analysis S4: analyzing the at least one detection signal to obtaining the detection result data by the analysis unit 72.

In the sampling step S1, the sleeve 20 preferably keeps in a distance from the female genital between 1 cm and 30 cm so as to carry out contactless sampling and avoid input of non-analyte; the pump 40 starts pumping for a predetermined time and then stops pumping so that the analyte is detained in the detection chamber 111 to be detected; after the detection step S2, the pump 40 is restarted to pump clean gas into the detection chamber 111 (a clean step S5 shown in FIG. 9) so as to blow off the analyte to avoid pollution or interference on next detection. In this embodiment, the predetermined time in the sampling step S1 may be 10 seconds to 30 seconds, and the clean gas in the clean step S5 may be continuously supplied for 10 seconds so as to have good clean effect. In the analysis step S4, the analysis unit 72 further converts the at least one detection signal into the gas graph and obtains the detection result data according to a comparison of the gas graph with the plurality of standard gas graphs so as to quickly and contactlessly detect and analyze the analyte for rapid diagnosis.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A gas detection system for gynecological disease detection, configured to detect an analyte from a female vagina, including:
a main body, including a body portion and a head portion protrudingly disposed on the body portion, the head portion having an intake channel disposed therethrough and configured to input the analyte, the body portion including a detection chamber communicated with the intake channel and an exhaust channel;
a sleeve, detachably sleeved to the head portion, including a through slot aligned with the intake channel;
a detector, including at least one sensor disposed in the detection chamber, the at least one sensor configured to detect at least one target of the analyte and produce at least one detection signal;
a pump, disposed on the main body and communicated respectively with the detection chamber and the exhaust channel; and
a controller, controlling operation of the detector and the pump, including a processing unit and a first communication unit communicated with the processing unit, the processing unit receiving the at least one detection signal and controlling the first communication unit to send the at least one detection signal.

2. The gas detection system for gynecological disease detection of claim 1, wherein at least one of the sleeve and the head portion has a filter corresponding to the intake channel.

3. The gas detection system for gynecological disease detection of claim 1, wherein the main body further includes a first housing, a second housing and a third housing disposed between the first housing and the second housing, and the first housing and the third housing define the detection chamber therebetween.

4. The gas detection system for gynecological disease detection of claim 1, wherein the main body further includes a receiving chamber and a first communication channel communicated between the detection chamber and the receiving chamber, the pump and the controller are disposed in the receiving chamber, and an inlet pipe of the pump is communicated with the first communication channel.

5. The gas detection system for gynecological disease detection of claim 4, wherein the main body further includes a second communication channel communicated between the receiving chamber and the exhaust channel, and an outlet pipe of the pump is communicated with the second communication channel.

6. The gas detection system for gynecological disease detection of claim 5, wherein a transitional chamber is disposed between the exhaust channel and the second communication channel.

7. The gas detection system for gynecological disease detection of claim 6, wherein at least one of the sleeve and the head portion has a filter covering the intake channel; at least one said filter is a membrane which is waterproof and gas permeable; at least one first sealing member is disposed between the sleeve and the head portion; the main body further includes a first housing, a second housing and a third housing disposed between the first housing and the second housing, and the first housing and the third housing define the detection chamber therebetween; a second sealing member is disposed between the first housing and the third housing, a shape of the second sealing member at least partially corresponds to shapes of the detection chamber, the receiving chamber and the transitional chamber; the gas detection system further includes a withdrawal mechanism disposed between the main body and the sleeve, the withdrawal mechanism includes an abutting member disposed on the body portion, and the abutting member is abuttable against the sleeve to move the sleeve in a direction remote from the head portion; the withdrawal mechanism further includes an elastic member abutted against and between the main body and the abutting member; the sleeve has a first engaging portion, and one of the abutting member and the head portion has a second engaging portion being engageable with the first engaging portion; the body portion includes a straight segment extending in an axial direction and a bent segment extending from the straight segment toward a side remote from the axial direction, and the head portion is integrally connected with the bent segment; the third housing has a first pillar located between the detection chamber and the receiving chamber and a second pillar located between the transitional chamber and the receiving chamber, the first pillar and the second pillar extend respectively toward the first housing, the first communication channel extends through the first pillar, the second communication channel extends through the second pillar; the second communication channel and the exhaust channel are lateral to each other and respectively communicated with the transitional chamber; the pump is a micropump; the controller further includes a power supply unit electrically connected with the processing unit, the power supply unit includes a battery received in the receiving chamber and an electrical interface configured to be connected with an external power source; and a third sealing member is disposed between the electrical interface and the main body.

8. The gas detection system for gynecological disease detection of claim 1, further including a withdrawal mechanism disposed between the main body and the sleeve, wherein the withdrawal mechanism includes an abutting member disposed on the body portion, and the abutting member is abuttable against the sleeve to move the sleeve in a direction remote from the head portion.

9. The gas detection system for gynecological disease detection of claim 1, wherein the body portion includes a straight segment extending in an axial direction and a bent segment extending from the straight segment toward a side remote from the axial direction, and the head portion is connected with the bent segment.

10. The gas detection system for gynecological disease detection of claim 1, further including an analysis unit communicated with the processing unit, wherein the analysis unit obtains a detection result data according to the at least one detection signal.

11. The gas detection system for gynecological disease detection of claim 10, further including an external device, wherein the external device includes the analysis unit and a second communication unit wirelessly communicated with the first communication unit.

12. A detection method, using the gas detection system for gynecological disease detection of claim 1, including following steps of:
  sampling: putting an end of the gas detection system with the sleeve to be close to a female genital and starting the pump to input the analyte into the detection chamber;
  detection: detecting the at least one target and producing the at least one detection signal by the detector;
  output: outputting the at least one detection signal to an analysis module; and
  analysis: analyzing the at least one detection signal to obtain a detection result data by the analysis module.

13. The detection method of claim 12, wherein in the sampling step, the pump starts pumping for a predetermined time and then stops pumping; after the detection step, the pump is restarted to pump clean gas into the detection chamber.

14. The detection method of claim 12, wherein in the sampling step, the sleeve keeps in a distance from the female genital between 1 cm and 30 cm.

\* \* \* \* \*